United States Patent
Merkel et al.

(10) Patent No.: US 8,916,733 B2
(45) Date of Patent: *Dec. 23, 2014

(54) PROCESSES FOR HYDROFLUORINATION OF 2-CHLORO-3,3,3-TRIFLUOROPROPENE TO 2-CHLORO-1,1,1,2-TETRAFLUOROPROPANE

(75) Inventors: Daniel C. Merkel, West Seneca, NY (US); Robert C. Johnson, Lancaster, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 1000 days.

This patent is subject to a terminal disclaimer.

(21) Appl. No.: 12/484,588

(22) Filed: Jun. 15, 2009

(65) Prior Publication Data

US 2009/0312585 A1 Dec. 17, 2009

Related U.S. Application Data

(60) Provisional application No. 61/073,186, filed on Jun. 17, 2008.

(51) Int. Cl.
*C07C 19/08* (2006.01)
*C07C 17/00* (2006.01)
*C07C 17/08* (2006.01)
*C07C 17/087* (2006.01)

(52) U.S. Cl.
CPC .................................. *C07C 17/087* (2013.01)
USPC .......................................... 570/167; 570/168

(58) Field of Classification Search
None
See application file for complete search history.

(56) References Cited

U.S. PATENT DOCUMENTS

| 5,616,819 A * | 4/1997 | Boyce et al. ............... 570/167 |
| 5,705,716 A * | 1/1998 | Li ................................ 570/134 |
| 5,905,174 A * | 5/1999 | Kanai et al. ............... 568/411 |
| 6,063,970 A | 5/2000 | Boyce et al. |
| 2010/0036179 A1 * | 2/2010 | Merkel et al. ............. 570/156 |

FOREIGN PATENT DOCUMENTS

| WO | WO 2007/079431 | 7/2007 |
| WO | WO2009003084 | 12/2008 |

OTHER PUBLICATIONS

March, J. Advanced Organic Chemistry 4$^{th}$ edition, 2001, 170.*
Partial European Search Report for application No. EP 09 16 2839.

* cited by examiner

*Primary Examiner* — Clinton Brooks
(74) *Attorney, Agent, or Firm* — Bruce Bradford

(57) ABSTRACT

A process for making 2-chloro-1,1,1,2-tetrafluoropropane. The process has the step of contacting 2-chloro-3,3,3-trifluoropropene with hydrogen fluoride in the presence of a catalyst having about 25 to about 99.9 mole percent antimony pentachloride and about 0.1 to about 75 mole percent of a metal of a Lewis acid under conditions sufficient to form the 2-chloro-1,1,1,2-tetrafluoropropane. There is a second process for making 2-chloro-1,1,1,2-tetrafluoropropane. The process has the step of hydrofluorinating about 75 to about 99.9 mole percent 2-chloro-3,3,3-trifluoropropene and about 0.1 to about 25 mole percent of one or more other hydrocarbons having at least one chlorine atom in the presence of a catalyst of fluorinated antimony pentachloride under conditions sufficient to form the 2-chloro-1,1,1,2-tetrafluoropropane. There is yet another process for hydrofluorinating 2-chloro-3,3,3-trifluoropropene to 2-chloro-1,1,1,2-tetrafluoropropane. The process has the step of contacting the 2-chloro-3,3,3-trifluoropropene with hydrogen fluoride in the presence of a vapor phase catalyst under conditions sufficient to form the 2-chloro-1,1,1,2-tetrafluoropropane.

29 Claims, No Drawings

PROCESSES FOR HYDROFLUORINATION OF 2-CHLORO-3,3,3-TRIFLUOROPROPENE TO 2-CHLORO-1,1,1,2-TETRAFLUOROPROPANE

CROSS-REFERENCE TO A RELATED APPLICATION

The present application claims priority based upon U.S. Provisional Application Ser. No. 61/073,186, filed Jun. 17, 2008, which is incorporated herein by reference in its entirety.

BACKGROUND OF THE INVENTION

1. Field of the Invention

The invention relates to processes for the hydrofluorination of 2-chloro-3,3,3-trifluoropropene(1233xf) to 2-chloro-1,1,1,2-tetrafluoropropane(244bb).

2. Description of the Related Art

Antimony halides have previously been described as useful as catalysts in the hydrofluorination of 1233xf to 244bb. Antimony pentachloride has been observed to be particularly active in catalyzing the hydrofluorination reaction (as disclosed in U.S. Provisional Patent Application 61/021,121, filed Jan. 22, 2008) but sometimes induces overfluorination of 1233xf to form pentafluoro compounds, such as 1,1,1,2,3-pentafluoropropane(245cb). 245cb has a lower boiling point than the desired 244bb product, which makes it difficult and costly to separate and remove. Antimony pentachloride can still be employed as a catalyst, but a lengthy induction or conditioning period is necessary to allow the catalyst to age.

It would be desirable to have a process for hydrofluorination of 1233xf to 244bb in which the induction period would be substantially reduced or eliminated. It would also be desirable to have a process for hydrofluorination of 1233xf to 244bb with improved yield and selectivity.

SUMMARY OF THE INVENTION

According to the present invention, there is a process for hydrofluorinating 2-chloro-3,3,3-trifluoropropene to 2-chloro-1,1,1,2-tetrafluoropropane. The process has the step of contacting the 2-chloro-3,3,3-trifluoropropene with hydrogen fluoride in the presence of a catalyst having about 25 to about 99.9 mole percent antimony pentachloride and about 0.1 to about 75 mole percent of a metal of a Lewis acid under conditions sufficient to form the 2-chloro-1,1,1,2-tetrafluoropropane. The metal of a Lewis acid is preferably selected from among $SbCl_3$, $TiCl_4$, $SnCl_4$, $TaCl_5$, $NbCl_5$, $NbCl_3$, $ZrCl_4$, and $HfCl_4$.

Further according to the present invention, there is a process for making 2-chloro-1,1,1,2-tetrafluoropropane. The process has the step of hydrofluorinating about 75 to about 99.9 mole percent 2-chloro-3,3,3-trifluoropropene and about 0.1 to about 25 mole percent of one or more other hydrocarbons having at least one chlorine atom in the presence of a catalyst of fluorinated antimony pentachloride under conditions sufficient to form the 2-chloro-1,1,1,2-tetrafluoropropane.

Still further according to the present invention, there is process for hydrofluorinating 2-chloro-3,3,3-trifluoropropene to 2-chloro-1,1,1,2-tetrafluoropropane, comprising contacting the 2-chloro-3,3,3-trifluoropropene with hydrogen fluoride in the presence of a vapor phase catalyst under conditions sufficient to form the 2-chloro-1,1,1,2-tetrafluoropropane.

DETAILED DESCRIPTION OF THE INVENTION

In the present invention, the problem of an overactive fluorinated antimony pentachloride ($SbCl_5$) catalyst is addressed by two techniques. The first technique is to intermix with the $SbCl_5$ a minor proportion of a fluorinated Lewis acid catalyst to moderate the reaction rate. The second technique is to admix a minor proportion of one or more other hydrocarbons having at least one chlorine atom with the 1233xf starting material. The hydrocarbons are underfluorinated relative to 1233xf and reduce the effective activity of the catalyst. Essentially, in the first technique, the composition of the catalyst is modified, and, in the second technique, the composition of the starting reactant is modified. The two techniques can be employed separately or in combination.

In the first technique, the fluorinated Lewis acid catalyst is intermixed with antimony pentachloride prior to fluorination such that the catalyst composition has about 25 mole percent to about 99.9 mole percent antimony pentachloride and about 0.1 mole percent to about 75 mole percent fluorinated Lewis acid catalyst. Preferably, the catalyst composition is about 50 mole percent to about 98 mole percent antimony pentachloride and about 2 mole percent to about 50 mole percent fluorinated Lewis acid catalyst. The fluorinated Lewis acid is preferably selected from among $SbCl_3$, $TiCl_4$, $SnCl_4$, $TaCl_5$, $NbCl_5$, $NbCl_3$, $ZrCl_4$, and $HfCl_4$. Most preferably, the catalyst composition is about 75 mole percent to about 95 mole percent antimony pentachloride and about 5 mole percent to about 25 mole percent fluorinated Lewis acid catalyst. The fluorinated Lewis acid is preferably selected from among $SbCl_3$, $TiCl_4$, $SnCl_4$, $TaCl_5$, $NbCl_5$, $NbCl_3$, $ZrCl_4$, and $HfCl_4$. Mixing of the antimony pentachloride and the fluorinated Lewis acid catalyst can be accomplished by any means known in the art.

In the second technique, the 1233xf reactant is admixed with a minor proportion of one or more other hydrocarbons containing at least one chlorine atom such that 1233xf is present from about 75 to about 99.9 mole percent and the one or more hydrocarbons are present from about 0.1 to about 25 mole percent. Preferably, the 1233xf is present from about 85 to about 99.5 mole percent and the one or more hydrocarbons are present from about 0.5 to about 15 mole percent. Most preferably, the 1233xf is present from about 90 to about 99 mole percent and the one or more hydrocarbons are present from about 1 to about 10 mole percent.

Useful other hydrocarbons include those containing at least one chlorine atom. Examples of hydrocarbons having at least one chlorine atom; 1,1,2,3-tetrachloropropene; 2,3-dichloro-3,3-difluoropropene; 2,3,3-trichloro-3-fluoropropene; and 1,1,1,2,3-pentachloropropane (HCC-240db). Also useful are those generating 2-chloro-3,3,3-trifluoropropene or 2-chloro-1,1,1,2-tetrafluoropropane. These compounds are particularly useful as they will all result in the desired 2-chloro-1,1,1,2-tetrafluoropropane or an intermediate that will convert to 2-chloro-1,1,1,2-tetrafluropropane.

For either technique, the hydrofluorination reaction is carried out under conditions sufficient to form 244bb (2-chloro-1,1,1,2-tetrafluoropropane). The reaction is preferably carried out at a temperature of about 30° C. to about 200° C., more preferably about 50° C. to about 150° C., and most preferably about 75° C. to about 125° C. The reaction is preferably carried out at a pressure of about 5 psia (pounds per square inch absolute) to about 200 psia, more preferably about 30 psia to about 175 psia, and most preferably about 60 psia to about 150 psia. The reaction is preferably carried out for a residence time of about 1 second to about 300 seconds, more preferably about 30 seconds to about 240 seconds, and most preferably about 40 seconds to about 120 seconds for a continuous process. The reaction can also be carried out in batch process. In case of using batch process, the reaction is preferably carried out for a residence time of about 15 second to about 3600 seconds, more preferably about 60 seconds to about 1800 seconds, and most preferably about 120 seconds to about 300 seconds. Residence time is the reactor volume that contains the liquid phase reactant mixture divided by the volumetric flow rate of the products.

For either technique, the by-product selectivity, i.e., selectivity for products other than the desired 244bb (2-chloro-1,1,1,2-tetrafluoropropane), is less than 15 mole percent, preferably less than 5 mole percent, and most preferably less than 1.5 mole percent.

When reaction is conducted in a vapor phase process, the catalyst may be supported or in bulk form (unsupported). Useful catalyst supports include carbon, alumina, fluorinated alumina, aluminum fluoride, alkaline earth metal oxides, fluorinated alkaline earth metals, zinc oxide, zinc fluoride, tin oxide, and tin fluoride.

The catalyst optionally may be activated prior to and during use. Useful activating agents include anhydrous hydrogen fluoride and chlorine. The catalyst is kept activated by the continuous or batch addition of an oxidizing agent such as $Cl_2$.

The hydrofluorination reaction may be carried out in the liquid phase or the vapor phase. Liquid-phase reactions are preferred.

The following are examples of the present invention and are not to be construed as limiting.

EXAMPLES

In the following examples, 2-chloro-3,3,3-trifluoropropene(1233xf) was fluorinated to 244bb. In Comparative Example 1, using a catalyst system of 100% antimony pentafluoride ($SbCl_5$). In Examples 1 and 2, a catalyst system of antimony pentachloride/antimony trichloride in a 5:1 mole ratio was substituted for the antimony pentafluoride catalyst system of Comparative Example 1. In Example 3, a 2% mix of 1,1,2,3-tetrachloropropene in 98% 2-chloro-3,3,3-trifluoropropene by weight is used early in the run to reduce the activity of the catalyst system, and thereby the formation of 1,1,1,2,2-pentafluoropropane. Example 4 demonstrates the use of vapor phase fluorination of 2-chloro-3,3,3-trifluoropropene to produce 244bb.

In Examples 1 and 2, the mixing of the antimony pentachloride/antimony trichloride was accomplished by adding a weighed amount of antimony pentachloride (liquid) first to a round-bottom flask equipped with a heating mantle, stirring bar, and condenser. A weighed amount of antimony trichloride (solid) was then added to the same flask. The flask was then heated to accomplish dissolution of the trichloride into the mixture and to exceed the melting point of the mixture (40-50 degrees Celsius). The molten catalyst mixture was then transferred to a heated (to prevent selective precipitation) cylinder. Nitrogen was added under pressure to the heated cylinder. The cylinder was connected to the reactor using a flexible tube. The contents of the cylinder was transferred to the reactor by opening a cylinder valve. The cylinder was weighed and compared to the cylinder's empty weight to ascertain that the desired weight transfer had been achieved. Hydrogen fluoride is added to the catalyst to achieve a fluorinated catalyst, which analysis will reveal is a mix of fluoride and chloride.

Comparative Example 1

Comparative Example 1 (Run #38) was a liquid phase fluorination of 2-chloro-3,3,3-trifluoropropene(1233xf) to 244bb using a catalyst system of antimony pentafluoride ($SbCl_5$). Comparative Example 1 demonstrated the effect of a long induction period when the run produced the 1,1,1,2,3-pentafluoropropane(245cb) byproduct in quantities of up to mole 50% by mole early in the Run, decreasing to reasonable levels (below ~1.5%) by mole after about 60 hours. Production of 245cb byproduct decreased with the age of the catalyst.

About 4175 grams of new $SbCl_5$ were added into Reactor R11. R11 is a Teflon™-lined liquid phase reactor (Teflon is a trademark of E.I. duPont de Nemours & Co) equipped with a 2-inch ID (inside diameter) catalyst stripper (a packed column to keep catalyst from escaping from the reactor system). The reactor is 2.75-inch ID×36-inch L (length). The reactor was heated to about 85° C.-87° C. HF feed was started first. After 1.3 lbs (pounds) of HF had been added to fluorinate the catalyst charge, the 2-chloro-3,3,3-trifluoropropene feed was started. The purity of the 2-chloro-3,3,3-trifluoropropene feed stock was about 98 GC Area % (gas chromatograph). The experiment ran continuously for about 136 hours. For this run, $Cl_2$ was fed batchwise about every 4 hours throughout the run in case needed to keep the catalyst active. The HF and 2-chloro-3,3,3-trifluoropropene feeds were varied during the run. The feeds averaged 0.495 lbs/hr (pounds/hour) HF, and 0.408 lbs/hr 2-chloro-3,3,3-trifluoropropene (chlorine was 5.4% by weight of organic) for a 7.9/1 ratio of HF/2-chloro-3,3,3-trifluoropropene, and 135 seconds residence time. In the middle of the run, the feeds averaged 0.843 lbs/hr HF and 0.66 lbs/hr 2-chloro-3,3,3-trifluoropropene (chlorine was 3.3% by weight of organic) for a 8.33/1 ratio of HF/2-chloro-3,3,3-trifluoropropene, and 80 seconds residence time. For the end of the run, the rate was increased. The feeds for this period averaged 1.42 lbs/hr HF and 1.24 lbs/hr 2-chloro-3,3,3-trifluoropropene (chlorine was 2% by weight of organic) for a 7.5/1 ratio of HF/2-chloro-3,3,3-trifluoropropene, and 47 seconds residence time. The reactor temperature range for the experiment was 78-91° C. and the pressure range was 85 psig-115 psig (pounds per square inch gauge). Results on a molar basis are set forth in Table 1 below.

TABLE 1

(Run #38, Conversion and Selectivity on a Molar Basis)

| hours el. Time | Temp ° C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd |
|---|---|---|---|---|---|---|---|---|---|
| 2.5 | 82.9 | 5.28 | 69.24 | 0.402 | 0.528 | 0.977 | 0.013 | 0.011 | 0.041 |
| 3.5 | 85.6 | 7.17 | 74.50 | 0.452 | 0.466 | 0.961 | 0.001 | 0.009 | 0.053 |
| 4.5 | 88 | 7.56 | 80.85 | 0.558 | 0.347 | 0.952 | 0.002 | 0.008 | 0.068 |
| 5.5 | 88.4 | 10.38 | 64.93 | 0.561 | 0.332 | 0.939 | 0.005 | 0.008 | 0.072 |
| 6.5 | 87.7 | 8.72 | 56.54 | 0.583 | 0.344 | 0.966 | 0.006 | 0.004 | 0.040 |
| 7.5 | 85.9 | 5.40 | 52.12 | 0.563 | 0.395 | 0.989 | 0.009 | 0.006 | 0.018 |
| 8.5 | 85.5 | 5.87 | 52.77 | 0.469 | 0.494 | 0.985 | 0.006 | 0.006 | 0.015 |
| 9.5 | 83.5 | 5.91 | 52.61 | 0.434 | 0.521 | 0.985 | 0.008 | 0.006 | 0.024 |
| 10.5 | 82 | 6.58 | 56.63 | 0.364 | 0.599 | 0.981 | 0.004 | 0.006 | 0.014 |
| 11.5 | 80.9 | 7.50 | 52.38 | 0.364 | 0.603 | 0.981 | 0.004 | 0.007 | 0.015 |
| 12.5 | 80.6 | 6.00 | 44.62 | 0.309 | 0.671 | 0.981 | 0.002 | 0.005 | 0.009 |
| 13.5 | 87.3 | 4.38 | 61.76 | 0.459 | 0.520 | 0.984 | 0.003 | 0.002 | 0.009 |
| 14.5 | 85 | 11.92 | 102.18 | 0.529 | 0.452 | 0.985 | 0.004 | 0.002 | 0.008 |
| 15.5 | 84.3 | 5.99 | 75.06 | 0.463 | 0.525 | 0.986 | 0.002 | 0.003 | 0.005 |
| 16.5 | 81.4 | 4.78 | 77.95 | 0.303 | 0.690 | 0.985 | 0.001 | 0.004 | 0.001 |

TABLE 1-continued (Run #38, Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd |
|---|---|---|---|---|---|---|---|---|---|
| 17.5 | 83.9 | 6.42 | 55.81 | 0.265 | 0.725 | 0.981 | 0.001 | 0.003 | 0.004 |
| 18.5 | 80.4 | 4.45 | 50.35 | 0.287 | 0.707 | 0.983 | 0.000 | 0.004 | 0.001 |
| 19.5 | 84 | 5.19 | 52.11 | 0.207 | 0.785 | 0.977 | 0.001 | 0.003 | 0.002 |
| 20.5 | 86.8 | 9.09 | 64.88 | 0.338 | 0.624 | 0.982 | 0.008 | 0.005 | 0.017 |
| 22.5 | 86 | 5.28 | 46.71 | 0.500 | 0.482 | 0.985 | 0.003 | 0.004 | 0.008 |
| 23.5 | 91.1 | 7.48 | 65.28 | 0.572 | 0.300 | 0.988 | 0.001 | 0.004 | 0.002 |
| 24.5 | 89.3 | 6.11 | 65.07 | 0.381 | 0.607 | 0.986 | 0.001 | 0.005 | 0.002 |
| 25.5 | 88 | 5.72 | 61.20 | 0.302 | 0.677 | 0.985 | 0.002 | 0.004 | 0.009 |
| 26.5 | 86.2 | 5.49 | 65.89 | 0.240 | 0.753 | 0.983 | 0.001 | 0.002 | 0.002 |
| 28.5 | 83.2 | 5.36 | 61.61 | 0.074 | 0.898 | 0.980 | 0.000 | 0.002 | 0.002 |
| 30.5 | 88.4 | 7.03 | 58.43 | 0.137 | 0.854 | 0.977 | 0.000 | 0.002 | 0.002 |
| 31.5 | 81.5 | 12.65 | 79.12 | 0.175 | 0.814 | 0.974 | 0.000 | 0.003 | 0.002 |
| 32.5 | 77.4 | 8.29 | 53.93 | 0.152 | 0.839 | 0.981 | 0.000 | 0.002 | 0.001 |
| 33.5 | 77.8 | 6.58 | 64.39 | 0.141 | 0.848 | 0.984 | 0.000 | 0.003 | 0.001 |
| 34.5 | 81.9 | 7.42 | 57.13 | 0.077 | 0.917 | 0.980 | 0.000 | 0.002 | 0.002 |
| 35.5 | 82 | 6.94 | 62.47 | 0.0605 | 0.9276 | 97.9 | 0.0008 | 0.0025 | 0.0069 |
| 36.5 | 81.7 | 7.47 | 56.94 | 0.1020 | 0.8732 | 97.6 | 0.0013 | 0.0036 | 0.0168 |
| 37.5 | 82.6 | 7.05 | 61.49 | 0.0437 | 0.9281 | 97.7 | 0.0011 | 0.0021 | 0.0158 |
| 38.5 | 84.1 | 6.63 | 56.90 | 0.0480 | 0.9382 | 97.7 | 0.0003 | 0.0016 | 0.0022 |
| 39.5 | 84.7 | 7.53 | 63.86 | 0.0507 | 0.9322 | 97.7 | 0.0002 | 0.0016 | 0.0018 |
| 40.5 | 85.8 | 6.42 | 59.09 | 0.0686 | 0.9205 | 97.0 | 0.0003 | 0.0017 | 0.0016 |
| 41.5 | 85.8 | 6.64 | 60.83 | 0.0874 | 0.8955 | 97.2 | 0.0011 | 0.0029 | 0.0056 |
| 42.5 | 86.7 | 6.90 | 66.22 | 0.0598 | 0.9292 | 97.6 | 0.0003 | 0.0020 | 0.0031 |
| 43.5 | 85.3 | 6.06 | 64.12 | 0.0480 | 0.9433 | 97.3 | 0.0002 | 0.0017 | 0.0015 |
| 45.5 | 81.6 | 3.75 | 54.60 | 0.0176 | 0.9756 | 97.8 | 0.0002 | 0.0020 | 0.0023 |
| 47.5 | 82.6 | 4.35 | 62.86 | 0.0212 | 0.9664 | 97.7 | 0.0002 | 0.0018 | 0.0017 |
| 47.5 | 82.9 | 6.61 | 87.62 | 0.0184 | 0.9719 | 97.7 | 0.0002 | 0.0014 | 0.0013 |
| 48.5 | 83.4 | 15.10 | 132.60 | 0.0235 | 0.9655 | 97.8 | 0.0003 | 0.0014 | 0.0012 |
| 50.5 | 81.8 | 3.52 | 48.35 | 0.0136 | 0.9756 | 97.8 | 0.0000 | 0.0016 | 0.0015 |
| 51.5 | 82 | 4.66 | 51.54 | 0.0155 | 0.9729 | 97.5 | 0.0001 | 0.0018 | 0.0012 |
| 52.5 | 84.8 | 4.96 | 53.28 | 0.0203 | 0.9620 | 96.7 | 0.0011 | 0.0026 | 0.0063 |
| 53.5 | 86 | 4.67 | 61.03 | 0.0224 | 0.9648 | 96.5 | 0.0003 | 0.0022 | 0.0027 |
| 54.5 | 91.7 | 5.28 | 69.24 | 0.0171 | 0.9722 | 97.2 | 0.0003 | 0.0018 | 0.0013 |
| 55.5 | 86.8 | 4.37 | 78.61 | 0.0233 | 0.9564 | 97.6 | 0.0017 | 0.0024 | 0.0070 |
| 56.5 | 85.6 | 4.56 | 77.59 | 0.0208 | 0.9571 | 97.5 | 0.0010 | 0.0017 | 0.0124 |
| 57.5 | 84.5 | 4.91 | 62.45 | 0.0168 | 0.9734 | 97.4 | 0.0005 | 0.0017 | 0.0030 |
| 58.5 | 85.8 | 4.31 | 81.33 | 0.0181 | 0.9715 | 97.3 | 0.0004 | 0.0013 | 0.0021 |
| 35.5 | 82 | 6.94 | 62.47 | 0.0605 | 0.9276 | 97.9 | 0.0008 | 0.0025 | 0.0069 |
| 36.5 | 81.7 | 7.47 | 56.94 | 0.1020 | 0.8732 | 97.6 | 0.0013 | 0.0036 | 0.0168 |
| 37.5 | 82.6 | 7.05 | 61.49 | 0.0437 | 0.9281 | 97.7 | 0.0011 | 0.0021 | 0.0158 |
| 38.5 | 84.1 | 6.63 | 56.90 | 0.0480 | 0.9382 | 97.7 | 0.0003 | 0.0016 | 0.0022 |
| 39.5 | 84.7 | 7.53 | 63.86 | 0.0507 | 0.9322 | 97.7 | 0.0002 | 0.0016 | 0.0018 |
| 40.5 | 85.8 | 6.42 | 59.09 | 0.0686 | 0.9205 | 97.0 | 0.0003 | 0.0017 | 0.0016 |
| 41.5 | 85.8 | 6.64 | 60.83 | 0.0874 | 0.8955 | 97.2 | 0.0011 | 0.0029 | 0.0056 |
| 42.5 | 86.7 | 6.90 | 66.22 | 0.0598 | 0.9292 | 97.6 | 0.0003 | 0.0020 | 0.0031 |
| 43.5 | 85.3 | 6.06 | 64.12 | 0.0480 | 0.9433 | 97.3 | 0.0002 | 0.0017 | 0.0015 |
| 45.5 | 81.6 | 3.75 | 54.60 | 0.0176 | 0.9756 | 97.8 | 0.0002 | 0.0020 | 0.0023 |
| 47.5 | 82.6 | 4.35 | 62.86 | 0.0212 | 0.9664 | 97.7 | 0.0002 | 0.0018 | 0.0017 |
| 47.5 | 82.9 | 6.61 | 87.62 | 0.0184 | 0.9719 | 97.7 | 0.0002 | 0.0014 | 0.0013 |
| 48.5 | 83.4 | 15.10 | 132.60 | 0.0235 | 0.9655 | 97.8 | 0.0003 | 0.0014 | 0.0012 |
| 50.5 | 81.8 | 3.52 | 48.35 | 0.0136 | 0.9756 | 97.8 | 0.0000 | 0.0016 | 0.0015 |
| 51.5 | 82 | 4.66 | 51.54 | 0.0155 | 0.9729 | 97.5 | 0.0001 | 0.0018 | 0.0012 |
| 52.5 | 84.8 | 4.96 | 53.28 | 0.0203 | 0.9620 | 96.7 | 0.0011 | 0.0026 | 0.0063 |
| 53.5 | 86 | 4.67 | 61.03 | 0.0224 | 0.9648 | 96.5 | 0.0003 | 0.0022 | 0.0027 |
| 54.5 | 91.7 | 5.28 | 69.24 | 0.0171 | 0.9722 | 97.2 | 0.0003 | 0.0018 | 0.0013 |
| 55.5 | 86.8 | 4.37 | 78.61 | 0.0233 | 0.9564 | 97.6 | 0.0017 | 0.0024 | 0.0070 |
| 56.5 | 85.6 | 4.56 | 77.59 | 0.0208 | 0.9571 | 97.5 | 0.0010 | 0.0017 | 0.0124 |
| 57.5 | 84.5 | 4.91 | 62.45 | 0.0168 | 0.9734 | 97.4 | 0.0005 | 0.0017 | 0.0030 |
| 58.5 | 85.8 | 4.31 | 81.33 | 0.0181 | 0.9715 | 97.3 | 0.0004 | 0.0013 | 0.0021 |
| 59.5 | 85.1 | 7.04 | 77.61 | 0.0207 | 0.9673 | 97.6 | 0.0010 | 0.0018 | 0.0023 |
| 60.5 | 84.1 | 9.44 | 92.17 | 0.0143 | 0.9688 | 97.5 | 0.0009 | 0.0011 | 0.0060 |
| 61.5 | 83.3 | 5.68 | 79.80 | 0.0115 | 0.9769 | 97.5 | 0.0007 | 0.0014 | 0.0043 |
| 62.5 | 83.2 | 4.42 | 68.37 | 0.0116 | 0.9759 | 97.6 | 0.0000 | 0.0014 | 0.0034 |
| 63.5 | 83.2 | 4.52 | 63.10 | 0.0108 | 0.9604 | 97.7 | 0.0018 | 0.0017 | 0.0148 |
| 64.5 | 82.7 | 9.18 | 94.88 | 0.0107 | 0.9718 | 97.7 | 0.0009 | 0.0013 | 0.0083 |
| 65.5 | 81.8 | 9.79 | 86.54 | 0.0104 | 0.9744 | 97.5 | 0.0005 | 0.0011 | 0.0047 |
| 66.5 | 82.7 | 8.51 | 79.63 | 0.0100 | 0.9771 | 97.6 | 0.0004 | 0.0010 | 0.0021 |
| 67.5 | 84.5 | 7.67 | 72.39 | 0.0136 | 0.9810 | 97.5 | 0.0014 | 0.0009 | 0.0013 |
| 68.5 | 85 | 8.31 | 75.69 | 0.0127 | 0.9798 | 97.4 | 0.0006 | 0.0010 | 0.0027 |
| 69.5 | 84.6 | 7.28 | 78.32 | 0.0131 | 0.9805 | 97.4 | 0.0005 | 0.0009 | 0.0018 |
| 70.5 | 87.9 | 7.41 | 75.96 | 0.0119 | 0.9792 | 97.4 | 0.0003 | 0.0009 | 0.0019 |
| 71.5 | 84.2 | 3.23 | 82.17 | 0.0136 | 0.9594 | 97.5 | 0.0016 | 0.0012 | 0.0204 |
| 72.5 | 85.2 | 3.97 | 75.69 | 0.0132 | 0.9782 | 97.5 | 0.0004 | 0.0012 | 0.0026 |
| 73.5 | 85.7 | 5.23 | 65.87 | 0.0145 | 0.9755 | 97.3 | 0.0003 | 0.0013 | 0.0020 |

TABLE 1-continued (Run #38, Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd |
|---|---|---|---|---|---|---|---|---|---|
| 74.5 | 85.1 | 4.59 | 81.36 | 0.0143 | 0.9760 | 96.9 | 0.0003 | 0.0012 | 0.0018 |
| 75.4 | 82.9 | 10.88 | 84.53 | 0.0121 | 0.9781 | 97.0 | 0.0003 | 0.0012 | 0.0020 |
| 76 | 84.7 | 5.72 | 83.19 | 0.0120 | 0.9761 | 97.5 | 0.0011 | 0.0016 | 0.0033 |
| 77 | 84.2 | 4.54 | 69.59 | 0.0151 | 0.9670 | 97.4 | 0.0009 | 0.0013 | 0.0106 |
| 78 | 83.7 | 6.37 | 84.65 | 0.0145 | 0.9779 | 97.3 | 0.0004 | 0.0009 | 0.0026 |
| 80 | 81.8 | 6.31 | 80.21 | 0.0100 | 0.9855 | 97.7 | 0.0002 | 0.0010 | 0.0017 |
| 81 | 81.9 | 8.43 | 65.81 | 0.0084 | 0.9867 | 97.5 | 0.0006 | 0.0009 | 0.0018 |
| 82 | 80.6 | 8.36 | 61.56 | 0.0079 | 0.9807 | 97.6 | 0.0011 | 0.0013 | 0.0071 |
| 83 | 79.3 | 7.88 | 74.86 | 0.0110 | 0.9644 | 97.5 | 0.0029 | 0.0017 | 0.0178 |
| 84 | 82.5 | 7.46 | 63.51 | 0.0078 | 0.9577 | 97.6 | 0.0017 | 0.0014 | 0.0194 |
| 85 | 82.4 | 7.70 | 73.91 | 0.0079 | 0.9600 | 97.7 | 0.0016 | 0.0014 | 0.0181 |
| 85.5 | 82.1 | 9.70 | 79.88 | 0.0076 | 0.9761 | 97.7 | 0.0006 | 0.0013 | 0.0046 |
| 86 | 82.2 | 8.55 | 72.14 | 0.0069 | 0.9755 | 97.5 | 0.0005 | 0.0011 | 0.0024 |
| 87 | 82.3 | 7.48 | 65.28 | 0.0074 | 0.9766 | 97.5 | 0.0005 | 0.0011 | 0.0019 |
| 89.5 | 84.6 | 10.13 | 66.51 | 0.0072 | 0.9830 | 97.2 | 0.0008 | 0.0011 | 0.0030 |
| 90.5 | 84.9 | 10.66 | 79.39 | 0.0074 | 0.9822 | 97.4 | 0.0004 | 0.0009 | 0.0016 |
| 92.5 | 84.2 | 7.99 | 60.49 | 0.0087 | 0.9743 | 97.5 | 0.0066 | 0.0009 | 0.0019 |
| 93.5 | 84.3 | 4.64 | 54.84 | 0.0066 | 0.9872 | 97.2 | 0.0004 | 0.0010 | 0.0016 |
| 94.5 | 83.8 | 5.09 | 58.42 | 0.0069 | 0.9871 | 97.3 | 0.0003 | 0.0010 | 0.0012 |
| 96.5 | 82.6 | 4.91 | 56.99 | 0.0075 | 0.9824 | 97.0 | 0.0005 | 0.0011 | 0.0045 |
| 97.5 | 82.3 | 5.97 | 62.30 | 0.0062 | 0.9886 | 97.4 | 0.0002 | 0.0011 | 0.0012 |
| 99.5 | 80.3 | 5.61 | 57.78 | 0.0062 | 0.9891 | 97.4 | 0.0003 | 0.0010 | 0.0020 |
| 100.5 | 80.4 | 5.93 | 60.90 | 0.0043 | 0.9899 | 97.3 | 0.0002 | 0.0015 | 0.0029 |
| 103.7 | 80.5 | 5.74 | 63.18 | 0.0049 | 0.9838 | 97.1 | 0.0002 | 0.0013 | 0.0019 |
| 106 | 82.2 | 12.23 | 81.85 | 0.0055 | 0.9855 | 96.8 | 0.0006 | 0.0010 | 0.0042 |
| 107 | 84.3 | 6.96 | 56.74 | 0.0053 | 0.9889 | 95.3 | 0.0000 | 0.0010 | 0.0012 |
| 108 | 84.3 | 4.97 | 74.03 | 0.0095 | 0.9750 | 92.5 | 0.0012 | 0.0015 | 0.0095 |
| 109 | 86.5 | 4.67 | 77.77 | 0.0120 | 0.9719 | 94.1 | 0.0009 | 0.0015 | 0.0109 |
| 110 | 86 | 5.60 | 70.37 | 0.0073 | 0.9851 | 96.0 | 0.0004 | 0.0011 | 0.0033 |
| 111 | 85.5 | 5.50 | 73.61 | 0.0066 | 0.9880 | 96.6 | 0.0001 | 0.0015 | 0.0015 |
| 112 | 83.4 | 5.45 | 69.12 | 0.0067 | 0.9687 | 97.0 | 0.0031 | 0.0016 | 0.0139 |
| 113 | 83.8 | 6.11 | 65.68 | 0.0049 | 0.9820 | 97.4 | 0.0006 | 0.0011 | 0.0054 |
| 114 | 83.3 | 5.86 | 74.89 | 0.0053 | 0.9859 | 97.4 | 0.0004 | 0.0011 | 0.0029 |
| 115 | 82.5 | 6.11 | 76.87 | 0.0042 | 0.9846 | 97.4 | 0.0003 | 0.0012 | 0.0019 |
| 116 | 82.6 | 3.85 | 84.01 | 0.0056 | 0.9753 | 97.4 | 0.0011 | 0.0009 | 0.0136 |
| 117 | 83.8 | 3.05 | 71.88 | 0.0053 | 0.9847 | 97.4 | 0.0005 | 0.0010 | 0.0056 |
| 120.2 | 83.7 | 4.74 | 54.08 | 0.0158 | 0.9744 | 97.3 | 0.0014 | 0.0006 | 0.0040 |
| 122.2 | 84.5 | 8.96 | 48.74 | 0.0136 | 0.9674 | 96.8 | 0.0023 | 0.0009 | 0.0117 |
| 123.2 | 83.9 | 6.82 | 52.42 | 0.0129 | 0.9720 | 96.6 | 0.0015 | 0.0009 | 0.0087 |
| 124.2 | 83.2 | 6.67 | 52.11 | 0.0136 | 0.9731 | 96.0 | 0.0013 | 0.0009 | 0.0068 |
| 125.2 | 83.7 | 7.27 | 51.45 | 0.0128 | 0.9735 | 93.8 | 0.0016 | 0.0010 | 0.0062 |
| 126.2 | 82.9 | 7.34 | 49.36 | 0.0113 | 0.9671 | 92.2 | 0.0025 | 0.0012 | 0.0127 |
| 127.2 | 82.5 | 6.15 | 59.07 | 0.0133 | 0.9686 | 85.3 | 0.0020 | 0.0013 | 0.0094 |
| 128.2 | 84.2 | 6.30 | 61.03 | 0.0152 | 0.9664 | 83.4 | 0.0020 | 0.0013 | 0.0083 |
| 129 | 86.6 | 4.84 | 88.11 | 0.0137 | 0.9471 | 83.7 | 0.0056 | 0.0016 | 0.0061 |
| 129.7 | 85.8 | 6.42 | 58.11 | 0.0144 | 0.9629 | 84.7 | 0.0032 | 0.0013 | 0.0061 |
| 131.2 | 85.6 | 12.30 | 74.60 | 0.0144 | 0.9645 | 82.4 | 0.0039 | 0.0014 | 0.0078 |
| 132.5 | 85.2 | 10.24 | 72.82 | 0.0055 | 0.9791 | 48.1 | 0.0000 | 0.0017 | 0.0069 |
| 134.3 | 85.9 | 7.64 | 75.01 | 0.0046 | 0.9849 | 53.9 | 0.0010 | 0.0016 | 0.0025 |
| 135.5 | 85.2 | 6.66 | 72.78 | 0.0038 | 0.9521 | 43.1 | 0.0000 | 0.0015 | 0.0356 |

Example 1

In Example 1, a catalyst system of $SbCl_5/SbCl_3$ in a 5:1 mole ratio was employed. About 1988 grams of new $SbCl_5$ were mixed with about 280 grams of new $SbCl_3$. The mixture was heated to achieve homogeneity. The combined mix was added into Reactor R11. R11 is a Teflon™-lined liquid phase reactor (Teflon is a trademark of E. I. duPont de Nemours & Co) equipped with a 2-inch ID (inside diameter) catalyst stripper (a packed column to keep catalyst from escaping from the reactor system). The reactor is 2.75-inch ID×36-inch L (length). The reactor was heated to about 85° C.-87° C. HF feed was started first. After 1.3 lbs (pounds) of HF had been added to fluorinate the catalyst charge, the 2-chloro-3,3,3-trifluoropropene feed was started. The purity of the 2-chloro-3,3,3-trifluoropropene feed stock was about 98 GC area % (gas chromatograph). The experiment (Run#47) ran continuously for about 14 hours. For this run, $Cl_2$ was fed batchwise about every 4 hours throughout the run in case needed to keep the catalyst active. The HF and 2-chloro-3,3,3-trifluoropropene feeds were varied during the run. Overall, the feeds averaged 1.09 lbs/hr HF (0.93 lbs/hr in the early portion of the run, 1.18 lbs/hr in the middle portion of the run, and 1.16 lbs/hr in the latter portion of the run), and 0.84 lbs/hr 2-chloro-3,3,3-trifluoropropene (1.07 lbs/hr in the early portion of the run, 0.6 lbs/hr in the middle portion, and 0.86 lbs/hr in the latter portion of the run) (chlorine was 5.4% by weight of organic) for a 12.4/1 ratio of HF/2-chloro-3,3,3-trifluoropropene and 82 seconds residence time. The reactor temperature range for the experiment was 85-100° C. and the pressure range was 85 psig-115 psig (pounds per square inch gauge). The results are set forth in Table 2 below.

TABLE 2

(Run #47 Conversion and Selectivity on a Molar Basis)

| hours el. Time | Temp °C. | HF/Org mole ration | Residence Time, seconds | molar selecctivity 245cb | molar selecctivity 244bb | molar Conversion 1233xf | molar selecctivity 235da | molar selecctivity 1232xf | molar selecctivity 1223xd | molar selecctivity others* |
|---|---|---|---|---|---|---|---|---|---|---|
| 1.1 | 77 | 5.65 | 90.69 | 0.0129 | 0.9683 | 0.6577 | 0.0025 | 0.0036 | 0.0012 | 0.0116 |
| 2.1 | 117 | 4.59 | 63.79 | 0.1134 | 0.8588 | 0.7150 | 0.0161 | 0.0057 | 0.0001 | 0.0059 |
| 3.1 | 96.6 | 5.10 | 80.29 | 0.1298 | 0.8472 | 0.8543 | 0.0007 | 0.0126 | 0.0062 | 0.0035 |
| 4.1 | 86.6 | 6.41 | 65.09 | 0.0277 | 0.9660 | 0.9578 | 0.0004 | 0.0024 | 0.0001 | 0.0035 |
| 5.1 | 85.7 | 8.25 | 76.84 | 0.0466 | 0.9417 | 0.9572 | 0.0014 | 0.0053 | 0.0001 | 0.0049 |
| 6.7 | 98.8 | 7.44 | 62.39 | 0.0152 | 0.9755 | 0.9718 | 0.0008 | 0.0057 | 0.0001 | 0.0027 |
| 7 | 85.6 | 40.89 | 152.73 | 0.0276 | 0.9381 | 0.7110 | 0.0103 | 0.0054 | 0.0100 | 0.0086 |
| 8 | 85.8 | 13.63 | 72.50 | 0.0128 | 0.9616 | 0.5798 | 0.0039 | 0.0062 | 0.0082 | 0.0073 |
| 9 | 86 | 9.62 | 100.58 | 0.0093 | 0.9695 | 0.5540 | 0.0038 | 0.0031 | 0.0064 | 0.0078 |
| 10 | 86.2 | 10.24 | 88.52 | 0.0097 | 0.9676 | 0.5328 | 0.0041 | 0.0032 | 0.0056 | 0.0097 |
| 11.4 | 86.6 | 35.59 | 77.48 | 0.0135 | 0.9517 | 0.9933 | 0.0187 | 0.0036 | 0.0008 | 0.0117 |
| 12.2 | 97.7 | 11.85 | 61.27 | 0.0051 | 0.9867 | 0.6298 | 0.0020 | 0.0025 | 0.0004 | 0.0033 |
| 13.2 | 99.7 | 7.45 | 67.40 | 0.0071 | 0.9768 | 0.5355 | 0.0028 | 0.0061 | 0.0018 | 0.0055 |
| 14.2 | 99 | 6.95 | 89.20 | 0.0064 | 0.9832 | 0.4921 | 0.0008 | 0.0023 | 0.0026 | 0.0046 |

The bold lines indicate periods of shut-down followed by re-start

Example 2

In Example 2, a catalyst system of SbCl$_5$/SbCl$_3$ in a 5:1 mole ratio was employed. About 1937 grams of new SbCl$_5$ were mixed with about 292 grams of new SbCl3. The mixture was heated to achieve homogeneity. The combined mixture was added into Reactor R11. R11 is a Teflon™-lined liquid phase reactor (Teflon is a trademark of E. I. duPont de Nemours & Co) equipped with a 2-inch ID (inside diameter) catalyst stripper (a packed column to keep catalyst from escaping from the reactor system). The reactor is 2.75-inch ID×36-inch L (length). The reactor was heated to about 85° C.-87° C. HF feed was started first. After 1.3 lbs (pounds) of HF had been added to fluorinate the catalyst charge, the 2-chloro-3,3,3-trifluoropropene feed was started. The purity of the 2-chloro-3,3,3-trifluoropropene feed stock was about 98 GC area % (gas chromatograph). The experiment (Run#48) ran continuously for about 129 hours. For this run, Cl$_2$ was fed batchwise about every 4 hours throughout the run in case needed to keep the catalyst active. The HF and 2-chloro-3,3,3-trifluoropropene feeds were varied slightly during the run. The feeds averaged 0.99 lbs/hr HF, and 0.72 lbs/hr 2-chloro-3,3,3-trifluoropropene (chlorine was 5.4% by weight of organic) for a 8.9/1 ratio of HF/2-chloro-3,3,3-trifluoropropene and 89 seconds residence The reactor temperature range for the experiment was 86-103° C. and the pressure range was 85 psig-115 psig (pounds per square inch gauge). Results are shown in Table 3 below.

TABLE 3

(Run #48 Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd | molar selectivity others* |
|---|---|---|---|---|---|---|---|---|---|---|
| 1 | 86.3 | 7.30 | 114.06 | 0.0036 | 0.9749 | 0.4650 | 0.0016 | 0.0037 | 0.0005 | 0.0156 |
| 1.5 | 88.1 | 11.96 | 147.31 | 0.0563 | 0.9011 | 0.7751 | 0.0026 | 0.0073 | 0.0010 | 0.0318 |
| 2.5 | 82.4 | 8.49 | 86.25 | 0.1391 | 0.8004 | 0.6165 | 0.0046 | 0.0025 | 0.0004 | 0.0530 |
| 3.5 | 85.5 | 13.05 | 114.85 | 0.1755 | 0.7593 | 0.5813 | 0.0067 | 0.0052 | 0.0003 | 0.0530 |
| 4.5 | 80.6 | 9.73 | 100.02 | 0.2206 | 0.7255 | 0.6609 | 0.0056 | 0.0065 | 0.0001 | 0.0417 |
| 5.5 | 75.6 | 12.17 | 89.06 | 0.3061 | 0.6602 | 0.7866 | 0.0043 | 0.0057 | 0.0001 | 0.0237 |
| 7.4 | 85.7 | 15.11 | 63.56 | 0.0898 | 0.7812 | 0.9651 | 0.0590 | 0.0356 | 0.0000 | 0.0344 |
| 8.4 | 90.3 | 10.46 | 77.98 | 0.3341 | 0.5772 | 0.9736 | 0.0087 | 0.0471 | 0.0001 | 0.0328 |
| 9.4 | 93.1 | 7.65 | 81.42 | 0.1529 | 0.7600 | 0.9757 | 0.0029 | 0.0315 | 0.0019 | 0.0508 |
| 10.4 | 98.4 | 8.30 | 78.56 | 0.1673 | 0.8147 | 0.9697 | 0.0005 | 0.0056 | 0.0013 | 0.0106 |
| 11.4 | 97.7 | 8.70 | 94.34 | 0.1583 | 0.8295 | 0.9699 | 0.0003 | 0.0033 | 0.0008 | 0.0078 |
| 12.4 | 96.1 | 9.39 | 90.98 | 0.1004 | 0.8896 | 0.9721 | 0.0003 | 0.0027 | 0.0006 | 0.0063 |
| 13.4 | 94.9 | 8.86 | 76.21 | 0.1077 | 0.8836 | 0.9727 | 0.0003 | 0.0025 | 0.0006 | 0.0054 |
| 14.4 | 96.3 | 9.54 | 74.48 | 0.0977 | 0.8955 | 0.9728 | 0.0002 | 0.0018 | 0.0006 | 0.0042 |
| 15.4 | 95.7 | 7.91 | 98.49 | 0.0863 | 0.9074 | 0.9733 | 0.0001 | 0.0016 | 0.0007 | 0.0040 |
| 16.4 | 97.1 | 10.88 | 84.53 | 0.0864 | 0.9066 | 0.9730 | 0.0001 | 0.0016 | 0.0009 | 0.0044 |
| 17.4 | 95.8 | 7.09 | 84.10 | 0.0817 | 0.9120 | 0.9728 | 0.0001 | 0.0016 | 0.0007 | 0.0039 |
| 18.4 | 96.4 | 9.39 | 90.98 | 0.0646 | 0.9297 | 0.9720 | 0.0001 | 0.0015 | 0.0008 | 0.0033 |
| 19.4 | 96 | 9.61 | 80.24 | 0.0513 | 0.9409 | 0.9721 | 0.0002 | 0.0019 | 0.0013 | 0.0045 |
| 20.4 | 97 | 7.87 | 89.27 | 0.0529 | 0.9399 | 0.9730 | 0.0002 | 0.0019 | 0.0012 | 0.0039 |
| 21.4 | 96.7 | 10.62 | 95.74 | 0.0490 | 0.9438 | 0.9724 | 0.0004 | 0.0019 | 0.0013 | 0.0036 |
| 22.4 | 98 | 9.71 | 67.12 | 0.0494 | 0.9399 | 0.9734 | 0.0001 | 0.0028 | 0.0027 | 0.0051 |

TABLE 3-continued (Run #48 Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd | molar selectivity others* |
|---|---|---|---|---|---|---|---|---|---|---|
| 23.4 | 97.4 | 9.11 | 105.04 | 0.0484 | 0.9448 | 0.9730 | 0.0002 | 0.0015 | 0.0013 | 0.0039 |
| 24.4 | 96.9 | 9.73 | 100.02 | 0.0507 | 0.9443 | 0.9732 | 0.0002 | 0.0014 | 0.0007 | 0.0027 |
| 25.4 | 96.5 | 7.64 | 75.01 | 0.0448 | 0.9495 | 0.9721 | 0.0001 | 0.0016 | 0.0012 | 0.0028 |
| 26.4 | 99.6 | 9.83 | 80.43 | 0.0441 | 0.9493 | 0.9728 | 0.0003 | 0.0015 | 0.0014 | 0.0035 |
| 27.4 | 97.3 | 8.58 | 85.84 | 0.0629 | 0.9326 | 0.9726 | 0.0002 | 0.0010 | 0.0007 | 0.0026 |
| 28.4 | 96.7 | 12.26 | 90.20 | 0.0584 | 0.9353 | 0.9720 | 0.0003 | 0.0014 | 0.0010 | 0.0036 |
| 29.4 | 96.5 | 7.73 | 81.05 | 0.0632 | 0.9318 | 0.9726 | 0.0001 | 0.0010 | 0.0008 | 0.0031 |
| 30.4 | 96.7 | 10.88 | 84.53 | 0.0597 | 0.9363 | 0.9728 | 0.0001 | 0.0008 | 0.0007 | 0.0023 |
| 31.4 | 95.6 | 9.54 | 91.70 | 0.0529 | 0.9434 | 0.9721 | 0.0001 | 0.0008 | 0.0007 | 0.0021 |
| 32.4 | 97.1 | 8.70 | 94.34 | 0.0527 | 0.9438 | 0.9723 | 0.0001 | 0.0008 | 0.0007 | 0.0020 |
| 33.4 | 92 | 9.70 | 79.88 | 0.0481 | 0.9486 | 0.9717 | 0.0001 | 0.0007 | 0.0006 | 0.0019 |
| 34.4 | 95.4 | 10.80 | 96.53 | 0.0388 | 0.9574 | 0.9706 | 0.0006 | 0.0006 | 0.0007 | 0.0019 |
| 35.4 | 95.3 | 8.16 | 72.87 | 0.0379 | 0.9577 | 0.9708 | 0.0007 | 0.0007 | 0.0009 | 0.0020 |
| 36.4 | 96.6 | 8.16 | 76.00 | 0.0357 | 0.9606 | 0.9687 | 0.0001 | 0.0007 | 0.0007 | 0.0021 |
| 37.4 | 88.7 | 9.83 | 80.43 | 0.0313 | 0.9643 | 0.9704 | 0.0001 | 0.0010 | 0.0010 | 0.0022 |
| 38.4 | 88 | 7.04 | 77.61 | 0.0365 | 0.9601 | 0.9708 | 0.0001 | 0.0007 | 0.0007 | 0.0019 |
| 39.4 | 87.6 | 10.88 | 84.53 | 0.0419 | 0.9538 | 0.9705 | 0.0005 | 0.0006 | 0.0009 | 0.0022 |
| 40.4 | 87.7 | 10.18 | 87.42 | 0.0392 | 0.9564 | 0.9705 | 0.0006 | 0.0006 | 0.0009 | 0.0022 |
| 41.4 | 87.9 | 9.12 | 83.43 | 0.0356 | 0.9594 | 0.9703 | 0.0006 | 0.0008 | 0.0012 | 0.0022 |
| 42.4 | 88.2 | 8.38 | 85.62 | 0.0335 | 0.9625 | 0.9717 | 0.0001 | 0.0007 | 0.0009 | 0.0022 |
| 43.4 | 88.3 | 9.73 | 100.02 | 0.0268 | 0.9675 | 0.9705 | 0.0006 | 0.0010 | 0.0016 | 0.0025 |
| 44.4 | 88.4 | 13.28 | 86.28 | 0.0236 | 0.9709 | 0.9704 | 0.0006 | 0.0010 | 0.0015 | 0.0024 |
| 45.4 | 89.9 | 7.67 | 89.03 | 0.0229 | 0.9718 | 0.9702 | 0.0006 | 0.0009 | 0.0014 | 0.0024 |
| 46.4 | 89.8 | 10.18 | 87.42 | 0.0227 | 0.9725 | 0.9708 | 0.0004 | 0.0009 | 0.0014 | 0.0021 |
| 47.4 | 89.9 | 11.39 | 92.28 | 0.0209 | 0.9731 | 0.9710 | 0.0004 | 0.0010 | 0.0020 | 0.0026 |
| 48.4 | 89.9 | 9.62 | 100.58 | 0.0214 | 0.9738 | 0.9711 | 0.0006 | 0.0009 | 0.0011 | 0.0021 |
| 49.4 | 91 | 8.70 | 94.34 | 0.0198 | 0.9758 | 0.9712 | 0.0005 | 0.0008 | 0.0010 | 0.0020 |
| 50.4 | 90.9 | 12.38 | 89.75 | 0.0199 | 0.9762 | 0.9703 | 0.0005 | 0.0008 | 0.0008 | 0.0018 |
| 51.4 | 91.1 | 7.14 | 91.77 | 0.0252 | 0.9718 | 0.9708 | 0.0001 | 0.0006 | 0.0007 | 0.0015 |
| 52.4 | 91.2 | 9.12 | 83.43 | 0.0221 | 0.9743 | 0.9694 | 0.0001 | 0.0007 | 0.0008 | 0.0019 |
| 53.4 | 91.8 | 9.83 | 80.43 | 0.0240 | 0.9728 | 0.9706 | 0.0001 | 0.0006 | 0.0007 | 0.0018 |
| 54.4 | 90.9 | 13.05 | 114.85 | 0.0223 | 0.9744 | 0.9693 | 0.0001 | 0.0007 | 0.0007 | 0.0018 |
| 55.4 | 91.1 | 10.51 | 96.25 | 0.0228 | 0.9736 | 0.9702 | 0.0005 | 0.0006 | 0.0007 | 0.0019 |
| 56.4 | 91.4 | 11.59 | 93.02 | 0.0209 | 0.9755 | 0.9682 | 0.0007 | 0.0006 | 0.0005 | 0.0018 |
| 57 | 89.2 | NA | NA | 0.0041 | 0.9924 | 0.9252 | 0.0005 | 0.0012 | 0.0001 | 0.0017 |
| 58 | 92.2 | NA | NA | 0.0052 | 0.9923 | 0.9508 | 0.0006 | 0.0012 | 0.0002 | 0.0006 |
| 59 | 94.2 | NA | NA | 0.0047 | 0.9727 | 0.9514 | 0.0006 | 0.0201 | 0.0007 | 0.0013 |
| 60 | 96.1 | NA | NA | 0.0051 | 0.9889 | 0.9495 | 0.0004 | 0.0034 | 0.0005 | 0.0018 |
| 61 | 96.1 | NA | NA | 0.0055 | 0.9489 | 0.9356 | 0.0017 | 0.0384 | 0.0013 | 0.0043 |
| 62.6 | 91.3 | NA | NA | 0.2850 | 0.6857 | 0.9753 | 0.0027 | 0.0172 | 0.0005 | 0.0088 |
| 63.6 | 87.3 | NA | NA | 0.0152 | 0.9787 | 0.9484 | 0.0004 | 0.0016 | 0.0008 | 0.0034 |
| 64.6 | 93 | NA | NA | 0.0128 | 0.9807 | 0.9378 | 0.0007 | 0.0016 | 0.0008 | 0.0034 |
| 65.6 | 91.5 | NA | NA | 0.0123 | 0.9791 | 0.8523 | 0.0021 | 0.0028 | 0.0004 | 0.0033 |
| 66.7 | 92 | NA | NA | 0.0098 | 0.9790 | 0.9198 | 0.0014 | 0.0029 | 0.0024 | 0.0046 |
| 67.7 | 96.4 | NA | NA | 0.0103 | 0.9749 | 0.8596 | 0.0044 | 0.0023 | 0.0021 | 0.0061 |
| 68.7 | 96.5 | NA | NA | 0.0099 | 0.9676 | 0.9066 | 0.0018 | 0.0147 | 0.0009 | 0.0052 |
| 69.7 | 95.3 | NA | NA | 0.0099 | 0.9784 | 0.9177 | 0.0010 | 0.0046 | 0.0010 | 0.0051 |
| 70.7 | 94.9 | NA | NA | 0.0102 | 0.9722 | 0.8600 | 0.0044 | 0.0023 | 0.0021 | 0.0088 |
| 71.7 | 95.0 | NA | NA | 0.0092 | 0.9806 | 0.9299 | 0.0004 | 0.0020 | 0.0026 | 0.0052 |
| 73.1 | 75.2 | NA | NA | 0.0075 | 0.9849 | 0.8190 | 0.0014 | 0.0009 | 0.0012 | 0.0041 |
| 74.1 | 93.9 | NA | NA | 0.0060 | 0.9843 | 0.8893 | 0.0006 | 0.0034 | 0.0004 | 0.0054 |
| 76.2 | 85.4 | 8.83 | 46.49 | 0.0642 | 0.8920 | 0.9202 | 0.0021 | 0.0246 | 0.0027 | 0.0143 |
| 77.2 | 82.6 | 13.22 | 63.51 | 0.3227 | 0.6648 | 0.9633 | 0.0006 | 0.0040 | 0.0016 | 0.0063 |
| 78.2 | 100 | 9.74 | 88.05 | 0.0700 | 0.9224 | 0.9774 | 0.0008 | 0.0024 | 0.0001 | 0.0043 |
| 79.2 | 99.9 | 6.53 | 88.05 | 0.1914 | 0.8007 | 0.9786 | 0.0004 | 0.0030 | 0.0004 | 0.0040 |
| 80.2 | 102.1 | 10.63 | 91.05 | 0.0786 | 0.9122 | 0.9760 | 0.0007 | 0.0046 | 0.0001 | 0.0039 |
| 81.2 | 101.6 | 9.01 | 86.28 | 0.0636 | 0.9260 | 0.9747 | 0.0006 | 0.0055 | 0.0003 | 0.0040 |
| 82.2 | 100.4 | 7.85 | 88.15 | 0.0548 | 0.9365 | 0.9740 | 0.0005 | 0.0041 | 0.0006 | 0.0036 |
| 83.2 | 100.6 | 10.97 | 84.13 | 0.0477 | 0.9434 | 0.9726 | 0.0005 | 0.0030 | 0.0014 | 0.0040 |
| 84.2 | 100.6 | 8.29 | 86.03 | 0.0398 | 0.9481 | 0.9747 | 0.0005 | 0.0020 | 0.0034 | 0.0064 |
| 85.2 | 100.7 | 8.70 | 94.34 | 0.0377 | 0.9519 | 0.9754 | 0.0005 | 0.0016 | 0.0028 | 0.0055 |
| 86.2 | 102.1 | 11.48 | 65.33 | 0.0367 | 0.9515 | 0.9751 | 0.0005 | 0.0017 | 0.0024 | 0.0073 |
| 87.4 | 102.5 | 11.89 | 55.41 | 0.0391 | 0.9532 | 0.9715 | 0.0001 | 0.0014 | 0.0021 | 0.0041 |
| 88.4 | 101.1 | 9.51 | 73.70 | 0.0411 | 0.9513 | 0.9701 | 0.0001 | 0.0015 | 0.0018 | 0.0043 |
| 89.4 | 100.8 | 7.01 | 72.05 | 0.0364 | 0.9572 | 0.9734 | 0.0004 | 0.0014 | 0.0010 | 0.0037 |
| 90.4 | 101.2 | 11.54 | 83.17 | 0.0351 | 0.9577 | 0.9737 | 0.0004 | 0.0015 | 0.0014 | 0.0039 |
| 91.4 | 100.6 | 9.83 | 80.43 | 0.0228 | 0.9662 | 0.9754 | 0.0004 | 0.0022 | 0.0030 | 0.0054 |
| 92.4 | 100.2 | 7.95 | 67.55 | 0.0193 | 0.9702 | 0.9758 | 0.0004 | 0.0021 | 0.0028 | 0.0053 |
| 93.4 | 100.6 | 11.04 | 85.15 | 0.0229 | 0.9676 | 0.9758 | 0.0003 | 0.0020 | 0.0026 | 0.0046 |
| 94.4 | 100.3 | 10.18 | 87.42 | 0.0225 | 0.9696 | 0.9759 | 0.0004 | 0.0016 | 0.0019 | 0.0041 |
| 95.4 | 100.3 | 9.67 | 71.32 | 0.0196 | 0.9694 | 0.9759 | 0.0004 | 0.0020 | 0.0031 | 0.0055 |
| 96.4 | 100.1 | 9.56 | 83.86 | 0.0220 | 0.9696 | 0.9753 | 0.0004 | 0.0016 | 0.0019 | 0.0046 |
| 97.4 | 99.8 | 10.27 | 76.61 | 0.0204 | 0.9720 | 0.9763 | 0.0001 | 0.0017 | 0.0021 | 0.0036 |
| 98.4 | 100.2 | 13.05 | 85.65 | 0.0190 | 0.9718 | 0.9760 | 0.0004 | 0.0019 | 0.0023 | 0.0046 |

TABLE 3-continued (Run #48 Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd | molar selectivity others* |
|---|---|---|---|---|---|---|---|---|---|---|
| 99.4 | 100.3 | 12.16 | 72.01 | 0.0249 | 0.9696 | 0.9746 | 0.0001 | 0.0014 | 0.0013 | 0.0027 |
| 100.4 | 100.5 | 11.40 | 76.66 | 0.0286 | 0.9659 | 0.9754 | 0.0001 | 0.0004 | 0.0013 | 0.0037 |
| 101.4 | 100.8 | 15.75 | 98.37 | 0.0251 | 0.9689 | 0.9756 | 0.0001 | 0.0014 | 0.0014 | 0.0031 |
| 102.4 | 100.9 | 10.60 | 78.50 | 0.0245 | 0.9702 | 0.9752 | 0.0001 | 0.0013 | 0.0011 | 0.0028 |
| 103.4 | 101.1 | 10.48 | 93.20 | 0.0261 | 0.9688 | 0.9755 | 0.0001 | 0.0013 | 0.0011 | 0.0027 |
| 104.4 | 100.8 | 12.80 | 98.25 | 0.0235 | 0.9708 | 0.9755 | 0.0001 | 0.0015 | 0.0013 | 0.0028 |
| 105.4 | 100.9 | 13.18 | 98.54 | 0.0232 | 0.9707 | 0.9761 | 0.0001 | 0.0016 | 0.0016 | 0.0028 |
| 106.4 | 101 | 11.39 | 92.28 | 0.0246 | 0.9695 | 0.9760 | 0.0001 | 0.0014 | 0.0016 | 0.0029 |
| 107.4 | 100.9 | 9.79 | 86.54 | 0.0236 | 0.9707 | 0.9764 | 0.0001 | 0.0013 | 0.0014 | 0.0029 |
| 108.4 | 100.9 | 12.92 | 101.64 | 0.0232 | 0.9712 | 0.9762 | 0.0001 | 0.0013 | 0.0013 | 0.0029 |
| 109.4 | 101.2 | 11.82 | 72.14 | 0.0148 | 0.9757 | 0.9755 | 0.0001 | 0.0020 | 0.0026 | 0.0048 |
| 110.4 | 101.3 | 6.68 | 80.24 | 0.0150 | 0.9755 | 0.9753 | 0.0001 | 0.0020 | 0.0025 | 0.0048 |
| 111.4 | 101.7 | 7.59 | 82.75 | 0.0153 | 0.9767 | 0.9757 | 0.0001 | 0.0018 | 0.0021 | 0.0040 |
| 112.4 | 102.6 | 6.73 | 74.00 | 0.0145 | 0.9765 | 0.9725 | 0.0001 | 0.0020 | 0.0024 | 0.0045 |
| 113.4 | 102.7 | 11.48 | 93.50 | 0.0118 | 0.9779 | 0.9736 | 0.0001 | 0.0022 | 0.0029 | 0.0051 |
| 114.4 | 102.4 | 8.20 | 78.03 | 0.0155 | 0.9764 | 0.9745 | 0.0001 | 0.0018 | 0.0020 | 0.0042 |
| 115.4 | 102.6 | 9.84 | 90.31 | 0.0157 | 0.9772 | 0.9747 | 0.0001 | 0.0016 | 0.0017 | 0.0038 |
| 116.4 | 102.7 | 9.15 | 78.96 | 0.0149 | 0.9777 | 0.9740 | 0.0001 | 0.0017 | 0.0019 | 0.0038 |
| 117.4 | 102.2 | 10.70 | 92.24 | 0.0143 | 0.9782 | 0.9728 | 0.0001 | 0.0018 | 0.0019 | 0.0038 |
| 118.4 | 103.3 | 8.77 | 96.93 | 0.0132 | 0.9763 | 0.9744 | 0.0001 | 0.0021 | 0.0025 | 0.0058 |
| 119.4 | 102 | 9.19 | 85.46 | 0.0126 | 0.9771 | 0.9751 | 0.0001 | 0.0024 | 0.0027 | 0.0051 |
| 120.4 | 102.8 | 10.32 | 104.19 | 0.0134 | 0.9772 | 0.9748 | 0.0001 | 0.0019 | 0.0025 | 0.0048 |
| 121.4 | 102.5 | 12.94 | 86.06 | 0.0132 | 0.9776 | 0.9752 | 0.0001 | 0.0019 | 0.0022 | 0.0050 |
| 122.4 | 102.6 | 10.78 | 81.22 | 0.0132 | 0.9796 | 0.9749 | 0.0001 | 0.0017 | 0.0018 | 0.0037 |
| 123.4 | 103.5 | 10.27 | 94.18 | 0.0155 | 0.9753 | 0.9689 | 0.0001 | 0.0019 | 0.0022 | 0.0051 |
| 124.4 | 104.6 | 10.24 | 99.21 | 0.0181 | 0.9768 | 0.9716 | 0.0001 | 0.0013 | 0.0010 | 0.0027 |
| 125.4 | 103.1 | 20.25 | 66.41 | 0.0171 | 0.9781 | 0.9697 | 0.0001 | 0.0012 | 0.0009 | 0.0026 |
| 126.4 | 103.5 | 9.73 | 100.02 | 0.0173 | 0.9772 | 0.9665 | 0.0003 | 0.0014 | 0.0011 | 0.0027 |
| 127.4 | 103.3 | 12.31 | 84.19 | 0.0166 | 0.9777 | 0.9733 | 0.0001 | 0.0016 | 0.0010 | 0.0031 |
| 128.4 | 102.6 | 14.89 | 101.73 | 0.0176 | 0.9772 | 0.9717 | 0.0001 | 0.0013 | 0.0011 | 0.0027 |
| 129.4 | 103.6 | 18.07 | 63.86 | 0.0164 | 0.9780 | 0.9662 | 0.0003 | 0.0013 | 0.0010 | 0.0030 |

Example 3

A 2% mix of 1,1,2,3-tetrachloropropene in 98% 2-chloro-3,3,3-trifluoropropene by weight is used early in the run to reduce the activity of the catalyst system, and, thereby, the formation of 1,1,1,2,2-pentafluoropropane. About 2261 grams of new SbCl$_5$ were added into Reactor R11. R11 is a Teflon™-lined liquid phase reactor (Teflon is a trademark of E.I. duPont de Nemours & Co) equipped with a 2-inch ID (inside diameter) catalyst stripper (a packed column to keep catalyst from escaping from the reactor system). The reactor is 2.75-inch ID×36-inch L (length). The reactor was heated to about 85° C. -87° C. HF feed was started first. After 1.4 lbs (pounds) of HF had been added to fluorinate the catalyst charge, the 2-chloro-3,3,3-trifluoropropene feed was started. The experiment (Run#50) ran continuously for about 22 hours. The HF feed for the run averaged 1.36 lb/hr and the 2-chloro-3,3,3-trifluoropropene feed averaged 0.79 lb/hr. for a 11.2/1 ratio of HF/2-chloro-3,3,3-trifluoropropene, and 75.2 second residence time. Chlorine was added from time to time in either 2 or 4% by weight of organic amounts to keep the catalyst active in case needed. The reactor temperature range for the experiment was 85-97° C. and the pressure range was 85 psig-115 psig (pounds per square inch gauge). Results are shown in Table 4.

TABLE 4

(Run #50 Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd | molar selectivity others* |
|---|---|---|---|---|---|---|---|---|---|---|
| 1 | 76.8 | 6.39 | 47.33 | 0.0352 | 0.9125 | 0.4956 | 0.0052 | 0.0117 | 0.0007 | 0.0346 |
| 2 | 81.9 | 9.07 | 61.06 | 0.0421 | 0.9168 | 0.6217 | 0.0034 | 0.0106 | 0.0004 | 0.0267 |
| 3 | 80.2 | 10.30 | 60.38 | 0.0305 | 0.9591 | 0.9152 | 0.0008 | 0.0026 | 0.0003 | 0.0067 |
| 4 | 88.7 | 9.79 | 60.05 | 0.0314 | 0.9035 | 0.9603 | 0.0031 | 0.0403 | 0.0002 | 0.0215 |
| 5 | 91 | 10.92 | 60.50 | 0.0316 | 0.9283 | 0.9303 | 0.0004 | 0.0165 | 0.0015 | 0.0216 |
| 6 *2 | 92.1 | 9.65 | 64.43 | 0.0524 | 0.9198 | 0.8524 | 0.0004 | 0.0054 | 0.0019 | 0.0202 |
| 7 *3 | 91.9 | 10.25 | 58.67 | 0.0507 | 0.9141 | 0.9142 | 0.0005 | 0.0064 | 0.0031 | 0.0253 |
| 8 *2 | 91.1 | 11.52 | 66.81 | 0.0412 | 0.9201 | 0.9370 | 0.0003 | 0.0139 | 0.0027 | 0.0217 |
| 9 | 89.5 | 10.15 | 58.37 | 0.0283 | 0.9382 | 0.9585 | 0.0017 | 0.0146 | 0.0022 | 0.0150 |
| 10 | 90.3 | 12.66 | 61.94 | 0.0205 | 0.9355 | 0.9575 | 0.0001 | 0.0142 | 0.0039 | 0.0258 |
| 11 | 89.8 | 10.92 | 60.50 | 0.0227 | 0.9558 | 0.9622 | 0.0001 | 0.0040 | 0.0022 | 0.0152 |
| 12 | 89.8 | 10.58 | 59.57 | 0.0252 | 0.9505 | 0.9083 | 0.0002 | 0.0024 | 0.0028 | 0.0189 |
| 12.8 *1 | 89.8 | 105.05 | 101.37 | 0.0218 | 0.9484 | 0.9274 | 0.0002 | 0.0024 | 0.0029 | 0.0243 |
| 13.8 | 89.6 | 11.19 | 71.39 | 0.0240 | 0.9558 | 0.9067 | 0.0004 | 0.0017 | 0.0021 | 0.0161 |
| 14.8 *3 | 89.2 | 15.90 | 93.69 | 0.0225 | 0.9512 | 0.9221 | 0.0004 | 0.0018 | 0.0027 | 0.0214 |

TABLE 4-continued (Run #50 Conversion and Selectivity on a Molar Basis)

| hours el. Time | Temp °C. | HF/Org mole ratio | Residence Time, seconds | molar selectivity 245cb | molar selectivity 244bb | molar Conversion 1233xf | molar selectivity 235da | molar selectivity 1232xf | molar selectivity 1223xd | molar selectivity others* |
|---|---|---|---|---|---|---|---|---|---|---|
| 15.8 | 888.9 | 9.65 | 64.43 | 0.0187 | 0.9564 | 0.9095 | 0.0005 | 0.0028 | 0.0027 | 0.0190 |
| 17.3 *3 | 90.3 | 13.73 | 169.30 | 0.0174 | 0.9607 | 0.9067 | 0.0004 | 0.0022 | 0.0010 | 0.0182 |
| 18.3 | 90 | 15.69 | 87.22 | 0.0206 | 0.9633 | 0.8013 | 0.0003 | 0.0022 | 0.0011 | 0.0124 |
| 19.3 *3 | 89 | 12.08 | 112.24 | 0.0110 | 0.9584 | 0.8700 | 0.0004 | 0.0050 | 0.0036 | 0.0216 |
| 20.3 | 91.1 | 10.82 | 76.64 | 0.0117 | 0.9600 | 0.7583 | 0.0010 | 0.0033 | 0.0068 | 0.0172 |
| 21.3 *3 | 91 | 12.42 | 83.80 | 0.0044 | 0.9566 | 0.9350 | 0.0009 | 0.0190 | 0.0079 | 0.0111 |

*1 after Gasbag #12, switched from 2% TCP/1233xf to pure 1233xf
*2 single chlorine addition after Gasbags #5 and 7
*3 double chlorine addition after Gasbags #6, 14, 16, 18, and 20

Example 4

The vapor phase fluorination of the 2-chloro-3,3,3-trifluoropropene (1233xf)+HF→2-chloro-1,1,1,2-tetrafluoropropane(244bb) was carried out. The fluorination catalyst for the experiment was 50 wt % $SbCl_5$ impregnated on 50 wt % Calgon PCB activated carbon.

A total of 2272.6 grams (or about 2800 cc) was charged to two 2-inch vapor-phase pipe reactors in series and installed in a sand bath for controlled heating.

The catalyst was activated by adding a minimum of a 5:1 mole ratio of HF to $SbCl_5$, followed by a $Cl_2$ addition of a minimum of a 3:1 mole ratio of $Cl_2$ to $SbCl_5$. Finally, a large excess of HF was passed through the catalyst bed for 2 hours.

The reaction was run using cylinders of 2-chloro-3,3,3-trifluoropropene crude material as organic feed to produce 2-chloro-1,1,1,2-tetrafluoropropane. The reactor effluent was collected in the distillation column before removal of excess HF. During the experiment, a 93.5% conversion of 2-chloro-3,3,3-trifluoropropene was achieved. The maximum selectivity of 2-chloro-1,1,1,2-tetrafluoropropane achieved was 98.4% on a molar basis. The reaction ran continuously for 76.5 hrs without attempting catalyst regeneration with $Cl_2$. The catalyst began showing signs of deactivation after about 65 hours on-stream time. The reaction conditions and experimental data are shown below in Tables 1A and 1B.

TABLE 1A

| On-stream time (hrs) | T (°C.) | P (Mpa) | Catalyst | 1233xf feed rate (g/hr) | HF feed rate (g/hr) | HF:1233xf mole ratio | Catalyst (ml) | Contact Time (sec) |
|---|---|---|---|---|---|---|---|---|
| 1-23 | 72 | 0.33 | $SbCl_5$/C | 95.3 | 222.3 | 15.5 | 2800 | 99 |
| 23-29 | 72 | 0.33 | $SbCl_5$/C | 145.2 | 258.6 | 11.8 | 2800 | 84 |
| 29-42 | 72 | 0.33 | $SbCl_5$/C | 186.0 | 290.3 | 10.3 | 2800 | 74 |
| 42-53 | 74 | 0.33 | $SbCl_5$/C | 240.4 | 331.1 | 9.1 | 2800 | 64 |
| 53-60 | 76 | 0.33 | $SbCl_5$/C | 322.1 | 381.0 | 8.1 | 2800 | 54 |
| 60-65.5 | 77 | 0.33 | $SbCl_5$/C | 394.6 | 480.8 | 8.3 | 2800 | 43 |
| 65.5-73.5 | 80 | 0.33 | $SbCl_5$/C | 408.2 | 485.4 | 7.9 | 2800 | 42 |
| 73.5-76.5 | 79 | 0.33 | $SbCl_5$/C | 281.2 | 426.4 | 10.5 | 2800 | 49 |

TABLE 1B

| On-stream Time (hrs) | 1233xf conversion | Selectivities (molar basis) | | | | |
|---|---|---|---|---|---|---|
| | | 245cb | 244bb | 1232iso | 1223xd | others |
| 1-23 | 89.9 | 3.9 | 92.6 | NA | 0.1 | 3.2 |
| 23-29 | 93.2 | 1.6 | 96.4 | NA | 0.0 | 1.8 |
| 29-42 | 93.5 | 1.2 | 96.6 | NA | 0.0 | 2.0 |
| 42-53 | 92.0 | 1.1 | 96.9 | NA | 0.0 | 1.9 |
| 53-60 | 83.8 | 1.0 | 98.4 | 0.0 | 0.0 | 0.6 |
| 60-65.5 | 82.8 | 1.2 | 98.1 | 0.0 | 0.0 | 0.7 |
| 65.5-73.5 | 81.5 | 1.3 | 97.8 | 0.3 | 0.0 | 0.7 |
| 73.5-76.5 | 75.1 | 1.1 | 95.5 | 0.8 | 0.0 | 2.6 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims

What is claimed is:

1. A continuous process for hydrofluorinating 2-chloro-3,3,3-trifluoropropene to 2-chloro-1,1,1,2-tetrafluoropropane, comprising: contacting the 2-chloro-3,3,3-trifluoropropene with hydrogen fluoride in the presence of a catalyst having about 25 to about 99.9 mole percent antimony pentachloride and about 0.1 to about 75 mole percent of a metal of a Lewis acid under conditions sufficient to form the 2-chloro-1,1,1,2-tetrafluoropropane, wherein a conversion of greater than about 45 mole percent 2-chloro-3,3,3-trifluoropropene and a selectivity of less than about 15 mole percent for each by-product other than 2-chloro-1,1,1,2-tetrafluoropropane is achieved in less than 30 hours from initiation of the contacting step.

2. The process of claim 1, wherein the metal of a Lewis acid is selected from the group consisting of $SbCl_3$, $TiCl_4$, $SnCl_4$, $TaCl_5$, $NbCl_5$, $NbCl_3$, $ZrCl_4$, and $HfCl_4$.

3. The process of claim 1, wherein the Lewis acid is SbCl₃.

4. The process of claim 1, wherein the catalyst is fluorinated.

5. The process of claim 1, wherein the catalyst has about 50 to about 98 mole percent antimony pentachloride and about 2 to about 50 mole percent Lewis acid.

6. The process of claim 1, wherein the hydrofluorination is carried out at a temperature of about 30° C. to about 200° C.

7. The process of claim 1, wherein the hydrofluorination is carried with a residence time of from about 30 seconds to about 240 seconds.

8. The process of claim 1, wherein a conversion of greater than about 45 mole percent 2-chloro-3,3,3-trifluoropropene and a selectivity of less than about 15 mole percent for each by-product other than 2-chloro-1,1,1,2-tetrafluoropropane is achieved in less than about 15 hours from initiation of the contacting step.

9. The process of claim 1, wherein a conversion of greater than about 45 mole percent 2-chloro-3,3,3-trifluoropropene and a selectivity of less than about 15 mole percent for each by-product other than 2-chloro-1,1,1,2-tetrafluoropropane is achieved in less than 12.4 hours from initiation of the contacting step.

10. The process of claim 1, wherein a conversion of greater than about 45 mole percent 2-chloro-3,3,3-trifluoropropene and a selectivity of less than about 15 mole percent for each by-product other than 2-chloro-1,1,1,2-tetrafluoropropane is achieved in less than 3.1 hours from initiation of the contacting step.

11. A continuous process for making 2-chloro-1,1,1,2-tetrafluoropropane, comprising: hydrofluorinating about 75 to about 99.9 mole percent 2-chloro-3,3,3-trifluoropropene and about 0.1 to about 25 mole percent of one or more other hydrocarbons having at least one chlorine atom in the presence of a catalyst of antimony pentachloride under conditions sufficient to form the 2-chloro-1,1,1,2-tetrafluoropropane, wherein a conversion of greater than about 50 mole percent 2-chloro-1,1,1,2-tetrafluoropropane and a selectivity of less than about 15 mole percent for each by-product other than 2-chloro-1,1,1,2-tetrafluoropropane is achieved in less than 30 hours from initiation of the contacting step.

12. The process of claim 11, wherein the one or more hydrocarbons are selected from the group consisting of 1,1,2,3-tetrachloropropene; 2,3-dichloro-3,3-difluoropropene; 2,3,3-trichloro-3-fluoropropene; and 1,1,1,2,3-pentachloropropane.

13. The process of claim 12, wherein the one or more hydrocarbons is 1,1,2,3-tetrachloropropene.

14. The process of claim 11, wherein the hydrofluorination is carried out at a temperature of about 30° C. to about 200° C.

15. The process of claim 11, wherein the hydrofluorination is carried with a residence time of from about 30 seconds to about 240 seconds.

16. The process of claim 11, wherein the catalyst is fluorinated.

17. The process of claim 11, wherein a conversion of greater than about 50 mole percent 2-chloro-1,1,1,2-tetrafluoropropane and a selectivity of less than about 15 mole percent for each by-product other than 2-chloro-1,1,1,2-tetrafluoropropane is achieved in less than about 16 hours from initiation of the contacting step.

18. The process of claim 11, wherein a conversion of greater than about 50 mole percent 2-chloro-1,1,1,2-tetrafluoropropane and a selectivity of less than about 15 mole percent for each by-product other than 2-chloro-1,1,1,2-tetrafluoropropane is achieved in less than about 5 hours from initiation of the contacting step.

19. The process of claim 11, wherein a conversion of greater than about 50 mole percent 2-chloro-1,1,1,2-tetrafluoropropane and a selectivity of less than about 15 mole percent for each by-product other than 2-chloro-1,1,1,2-tetrafluoropropane is achieved in less than one hour from initiation of the contacting step.

20. A continuous process for hydrofluorinating 2-chloro-3,3,3-trifluoropropene to 2-chloro-1,1,1,2-tetrafluoropropane, comprising: contacting the 2-chloro-3,3,3-trifluoropropene with hydrogen fluoride in the presence of a vapor phase catalyst under conditions sufficient to form the 2-chloro-1,1,1,2-tetrafluoropropane, wherein a conversion of greater than about 80 mole percent 2-chloro-3,3,3-trifluoropropene and a selectivity of less than about 15 mole percent for each by-product other than 2-chloro-1,1,1,2-tetrafluoropropane is achieved in less than 30 hours from initiation of the contacting step.

21. The process of claim 20, wherein the catalyst is fluorinated.

22. The process of claim 20, wherein the catalyst has about 25 to about 99.9 mole percent antimony pentachloride and about 0.1 to about 75 mole percent Lewis acid.

23. The process of claim 20, wherein the 2-chloro-3,3,3-trifluoropropene is provided in the form of a feed stream having about 75 to about 99.9 mole percent 2-chloro-3,3,3-trifluoropropene and about 0.1 to about 25 mole percent of one or more other hydrocarbons having at least one chlorine atom.

24. The process of claim 20, wherein the hydrofluorination is carried out at a temperature of about 30° C. to about 200° C.

25. The process of claim 20, wherein the hydrofluorination is carried at a residence time of from about 10 seconds to about 240 seconds.

26. The process in claim 20, wherein the catalyst is supported.

27. The process in claim 23, wherein the catalyst support is selected from the group consisting of carbon, alumina, fluorinated alumina, aluminum fluoride, alkaline earth metal oxides, fluorinated alkaline earth metals, zinc oxide, zinc fluoride, tin oxide, and tin fluoride.

28. The process of claim 20, wherein the catalyst is activated prior to use.

29. The process of claim 20, wherein a conversion of greater than about 80 mole percent 2-chloro-3,3,3-trifluoropropene and a selectivity of less than about 15 mole percent for each by-product other than 2-chloro-1,1,1,2-tetrafluoropropane is achieved in less than 23 hours from initiation of the contacting step.

* * * * *